United States Patent [19]

Annis

[11] Patent Number: 4,809,312
[45] Date of Patent: Feb. 28, 1989

[54] METHOD AND APPARATUS FOR PRODUCING TOMOGRAPHIC IMAGES

[75] Inventor: Martin Annis, Cambridge, Mass.

[73] Assignee: American Science and Engineering, Inc., Cambridge, Mass.

[21] Appl. No.: 888,019

[22] Filed: Jul. 22, 1986

[51] Int. Cl.⁴ ............................................. G01N 23/20
[52] U.S. Cl. ................................... 378/146; 378/149; 378/6; 378/87
[58] Field of Search ...................... 378/86, 87, 88, 89, 378/90, 147, 149, 146, 6

[56] References Cited

U.S. PATENT DOCUMENTS

| | | |
|---|---|---|
| Re. 28,544 | 9/1975 | Stein et al. |
| 3,106,640 | 10/1963 | Oldendorf |
| 3,197,638 | 1/1963 | Sinclair ............................. 378/86 |
| 3,432,660 | 3/1969 | Anger ............................. 250/71.5 |
| 3,509,341 | 4/1970 | Hindel et al. ..................... 250/71.5 |
| 3,688,113 | 8/1972 | Miraldi ........................... 250/71.5 R |
| 3,769,507 | 10/1973 | Kenney et al. |
| 3,935,462 | 1/1976 | de Luca et al. |
| 3,936,638 | 2/1976 | Gibbons |
| 3,961,186 | 6/1976 | Leunbach |
| 3,973,127 | 8/1976 | Matsuda et al. |
| 3,976,885 | 8/1976 | Brunnett et al. |
| 3,978,336 | 8/1976 | Roux ................................. 250/366 |
| 3,979,594 | 9/1976 | Anger |
| 4,034,218 | 7/1977 | Turcotte |
| 4,124,804 | 11/1978 | Mirell |
| 4,136,283 | 1/1979 | Blum ................................. 250/363 |
| 4,229,651 | 10/1980 | Danos |
| 4,258,256 | 3/1981 | Harding |
| 4,277,686 | 7/1981 | Harding |
| 4,375,695 | 3/1983 | Harding et al. |
| 4,380,817 | 4/1983 | Harding et al. |
| 4,384,209 | 5/1983 | Wagner et al. |
| 4,423,522 | 12/1983 | Harding |
| 4,472,822 | 9/1984 | Swift |
| 4,480,332 | 10/1984 | Strecker |
| 4,495,636 | 1/1985 | Jacobs et al. |

FOREIGN PATENT DOCUMENTS 2461877 7/1986 Fed. Rep. of Germany ........ 378/87
1602521 3/1977 United Kingdom .

OTHER PUBLICATIONS

Moretti et al., "90° Compton Scattering Tomography. Its Implementation by Means of a Bar Detector Scintigraph", *The Journal of Nuclear Medicine and Allied Sciences*, vol. 24, No. 3-4, 1980, pp. 111-119.
Guzzardi et al., "90° Compton Scattering Tomography of the Lung: Detection Characteristics and Correction of the Attenuation", *The Journal of Nuclear Medicine and Allied Sciences*, vol. 24, No. 3-4, 1980, pp. 163-169.
Lale, "The Examination of Internal Tissues, Using Gamma-Ray Scatter with a Possible Extension to Megavoltage Radiography", *Journal of Physics in Medicine and Biology*, 1959, pp. 159 et seq.
Stein et al., "Flying Spot X-Ray Imaging Systems", *Materials Evaluation*, Jul. 1972, pp. 137 et seq.

Primary Examiner—Carolyn E. Fields
Assistant Examiner—Joseph A. Hynds
Attorney, Agent, or Firm—Pollock, Vande Sande & Priddy

[57] ABSTRACT

Method and apparatus for the production of tomographic images includes a flying spot scanner to form, from a beam of penetrating radiation, a pencil beam sweeping over a line in space to define a sweep plane. An object to be examined is supported so that the pencil beam intersects the object along a path passing through the object and a selected slice of the object. A line collimator is provided for filtering radiation scattered by the object, the line collimator has a field of view which intersects the sweep plane in a bounded line so that the line collimator passes only that radiation scattered by elementary volumes of the object lying along the bounded line. A radiation detector responds to that portion of the scattered radiation which is passed by the line collimator.

59 Claims, 5 Drawing Sheets

METHOD AND APPARATUS FOR PRODUCING TOMOGRAPHIC IMAGES

DESCRIPTION

1. Technical Field

The invention relates to the production of tomographic images using penetrating radiation.

2. Background Art

Imaging using penetrating radiation has been applied for the generation of images using a variety of techniques. The oldest technique produces an image (typically on x-ray film, although not necessarily) which is referred to as a shadowgraph. Because of the disadvantages of shadowgraphs, i.e. it gives a line of sight projection of the object whose image has been produced, improvements have long been sought. Tomography, i.e. the production of an image representing a slice or plane through an object being examined, has been a long-felt need. Techniques are available for the production of tomographic images or tomograms, although the presently known techniques all have various drawbacks.

One of those techniques is illustrated by Olendorf in U.S. Pat. No. 3,106,640. He mentions complicated mechanical techniques such as planigraphy, tomography, laminography and the like, which typically involve the synchronous motion, at identical angular rates, of a radiation source and a recording plate which is sensitive to the radiation. In principle, motion during the exposure period theoretically blurs everything not on a plane parallel to the plate and on the axis of rotation. This provides a sectional radiograph (or tomograph) of a layer of the object under consideration; however the layer has a vague and indefinite thickness. Thus, the mechanical isolation of the layer or section from other detail is quite poor. Other techniques similar to Olendorf are shown by Anger U.S. Pat. No. 3,979,594; Brunnett U.S. Pat. No. 3,976,885; Matsuda U.S. Pat. No. 3,973,127 and deLuca U.S. Pat. No. 3,935,462.

Since the 1970's, a far more popular tomographic technique and one which has achieved widespread success is referred to as computed tomography, relying in the main on the work of Hounsfield and Cormack, for which they jointly received a Nobel prize. While there are a variety of specific techniques comprehended under the term "computed tomography", for out purposes they can all be described together. In computed tomography, an object is illuminated by a beam of penetrating radiation (in some cases this is a fan beam illuminating the object from edge to edge, in other cases it might be one or a plurality of pencil beams). A detector or detectors records the x-ray energy emitted by the object as a result of the illumination. In some fashion or another, the entire slice is illuminated at a given angle, and then the angular relation between the object and the source/detector arrangement is altered and the process is repeated. This is repeated a relatively large number of times, so that the x-ray energy transmitted through the plane of interest is recorded through a plurality of paths and at a plurality of angles. This data is then used as the input to a computer which generates a cross-sectional image of the section of the object that had been illuminated.

Notwithstanding the popularity of computed tomography, there are a number of major disadvantages with this technique. Firstly, in order to obtain the desired image, the object must be illuminated from edge to edge and the x-ray response of the object throughout this region must be recorded. In other words, even if we are aware that out interest is centered on a particularly known region of a known slice of the object, the entire slice must be illuminated and the data taken from that entire slice must be used before we can produce the image that we desire. Secondly, the image is not produced in real time and in fact there is a delay while the computer portion of the equipment operates on the data that has been recorded before the image is available. The necessity for the rotation poses a number of disadvantages. In a very practical sense it limits the slice orientations athat are available. Consider for example the human body. Obtaining a slice which is essentially horizontal with respect to a vertically standing individual requires that relative rotation be effected about an axis which is vertical; this is the typical configuration of most popular machines. However, if one happens to desire a vertical slice relative to a vertical individual, then the human body must be rotated about a horizontal axis, i.e. the human body must be rotated head to foot. I do not know of any practical machines which are capable of this type of rotation. A significant limitation of computed tomography is the fact that the contrast in a region of the image which contrasts is ultimately limited by the statistical fluctuation or noise in that particular region depends upon the attenuation in every other region of the image. Specifically, it is a characteristic of CT that if there is a large attenuation of an x-ray beam traversing any part of the image, the entire image becomes more noisy.

It is a goal of the invention to provide a method and produce apparatus for generating tomographic images which eliminates the disadvantages of the prior art. More particularly, it is a specific goal of the invention to eliminate the vast computing power required as compared to the requirements of conventional computed tomography. It is another goal of the invention to produce tomographic images essentially in real time. It is a further goal of the invention to eliminate the mechanical equipment which is provided for the necessity of relative rotation as the sine qua non of any tomographic image. It is a further goal of the invention to produce tomographic images with less statistical noise and at lower radiation doses. Finally, it is a goal of the invention to produce a tomographic image which requires only illuminating or irradiating those portions of the object including the slice representing the desired image and eliminating the necessity for illuminating an object edge to edge regardless of the region of interest.

SUMMARY OF THE INVENTION

In accordance with the invention, a device useful in producing a tomographic image of a selected slice includes a source of penetrating radiation, typically this will be an x-ray source although other forms of penetrating radiation could be employed in lieu of x-rays. The radiation emitted by the source is operated on by a sweep means which performs two functions. It limits the energy emitted by the source into a narrow pencil beam, and it repeatedly sweeps this pencil beam over a line in space. Typically, the motion of the pencil beam is linear, i.e. confined to a plane, and as the beam is swept it traces the line in space just referred to. The object to be imaged is supported so that the sweeping pencil beam intersects the object along a transmit line which passes through the object and at the same time passes through the selected slice, i.e. the region within the object of interest.

While most of the prior art apparatus and techniques produce the tomographic images from the transmitted beam, i.e. from detecting the energy which is emitted from the object being imaged along the line of sight of the illuminating beam, there are prior art techniques which rely on scattered energy. Olendorf, for example, in FIG. 7 suggest using scattered energy. Another suggestion for using scattered energy in producing tomographic images is Lale, "The Examination of Internal Tissues Using Gamma Ray Scatter with a Possible Extension to Megavoltage Radiography", appearing in *Physics in Medicine and Biology,* 1959, at pages 159 et seq.

The present invention employs scattered and/or fluorescent energy as opposed to the transmitted ray. Accordingly, the invention includes a radiation detector which is responsive to radiation scattered from the object out of the line of sight of the illuminating beam. Without additional localization, however, energy at any instant could be scattered by any elementary volume within the object being imaged which lies along the transmit line, i.e. the line through the object traversed by the pencil beam. Because of uncertainty, data collected in that fashion would be of little or no value. Accordingly, the invention also employs a collimator located between the object being imaged and the radiation detector means. The collimator is referred to as a line collimator. The collimator is arranged to accept scattered energy which is scattered by any elementary volume lying within the object being imaged which iscentered or adjacent the plane defined by the sweeping motion of the pencil beam and simultaneously centered adjacent another plane, which is parallel to a reference surface of the collimator and a fixed distance therefrom. In effect, the intersection of these two planes defines a line and thus the collimator is referred to as a line collimator, since it selects, filters or admits energy scattered from volumes centered along or adjacent this preferential line. From another point of view, the sweep of the illuminating beam (a pencil beam) defines a sweep plane. The collimator has a field of view (the volume from which scattered energy will be passed on to the detector) which intersects the sweep plane in a bounded line. As such, only energy scattered from elementary regions of the object lying along the bounded line will be detected. The size of the volume is determined in part by the dimensions of the pencil beam and in part by the line collimator. The size of the pencil beam determines two dimensions of the elementary volume, those dimensions in a plane perpendicular to the line of sight of the beam, the third dimension of the volume is the dimension along the length of the beam. This latter dimension is controlled in part by the dimensions of the collimator, as will be described below. This dimension is the "slice thickness". At any instant, the pencil beam intersects the preferential line or line of focus or the slice at only one point, or at one elementary volume. Thus, while the line collimator rejects energy scattered from the object which is not centered along this line, there is only a single elementary volume along the preferential line which is illuminated. As a result, the scattered energy must come from this elementary volume, and no other. As the pencil beam sweeps over the line in space, it intersects a succession of points along the preferential line. The extent of the sweeping motion of the pencil beam is selected so that the succession of intersections completely traces out the preferential line. Accordingly, a time sequence of responses of the radiation detector means describes the sequence of elementary volumes from which the scattered energy is emitted.

The object being imaged is then moved relative to the source/detector. As a result, over time, there is a succession of preferential lines. The collection of these successive preferential lines defines the selected slice, i.e. that slice that will contribute to the image.

In a preferred embodiment, the radiation detector means may be a scintillator or equivalent device which produces optical energy in response to impinging x-ray energy. The optical energy is then converted in a manner known to those skilled in the art into electrical energy which may be used to intensity modulate an electron beam of a cathode ray tube. By coordinating the sweeping action of the pencil beam and the motion of the object relative to the source/detector, with the sweep of the cathode ray tube, an image of the selected slice is produced on the cathode ray tube. Alternatively and preferably, signals derived from the radiation detector means can be stored, preferably in digital form, for a later production of an image either on a cathode ray tube or a hard copy print.

Accordingly, the invention provides a device useful in producing a tomographic image of a selected slice lying in an object to be examined, comprising:

a source of penetrating radiation, sweep means responsive to energy emitted by said source for forming said energy into a pencil beam and for repeatedly sweeping said pencil beam over a line in space, first means for supporting an object to be examined so that said pencil beam intersects said object along a transmit line passing through said object and said selected slice, line collimating means for filtering radiation scattered by said object to pass only radiation scattered by elementary volumes of said object centered along a line defined by a succession of intersections between said transmit line and said selected slice, said line collimating means comprising plural channels, each of said channels being substantially planar to define plural channel planes, said channel planes intersecting said selected slice in said bounded line, and radiation detector means responsive to radiation passed by said line collimating means.

In one embodiment the relative motion of the object is mutually perpendicular to the plane of the pencil beam and the preferential line, the selected slice, as will be apparent, is essentially a plane which is swept out as the line collimator sees successive preferential lines. However, the invention is not confined to producing images of planar slices. Rather, the slice which is imaged may be of a variety of geometrical shapes so long as that shape is generated by the motion of a line. For example, the selected slice can be in the form of a right circular cylinder merely by changing the relative motion of the object and source/detector. To generate an image of a right circular slice, instead of translating the object in a direction which is mutually perpendicular to the plane of the pencil beam and the preferential line, the object is rotated about an axis parallel to but offset from the preferential line. To generate an image of a conical surface, the motion of the object is circular about an axis which intersects the preferential line. The object is tilted so that the preferential line passes through the axis of rotation at an angle which is ½ the included angle of the desired cone.

In order to increase the detection efficiency, the solid angle from which scattered energy is accepted is increased. This is effected by increasing the size (area) of both the line collimating means and the radiation detector means. In a preferred embodiment, the line collimating means and radiation detector means are located adjacent the same side of the object being imaged as is the source of penetrating radiation with the line collimating means and the radiation detector means located between the object being imaged and the source of penetrating radiation. In order to provide a path for the sweeping pencil beam, both the line collimating means and the radiation detector means are formed of a pair of line collimating elements and a pair of radiation detector elements, each lying on a different side of the pencil beam.

The line collimating means may be formed of a radiation absorbing structure which has a similar cross-section in many planes perpendicular to the plane defined by the sweeping beam. That cross-section includes a plurality of channels, each channel lying along an imaginary line terminating at the intersection of the pencil beam and the selected slice and extending through a first face of the line collimating means closer to the object than to the detector means, to a second face of the line collimating means closer to the detector means than to the object. The channels in effect are planar or substantially planar to define plural channel planes, the channel planes intersecting the selected slice in the bounded line.

In a practical embodiment, rather than viewing the intersection of the pencil beam and the selected slice as a point, it is actually an elementary volume, a small solid element centered on the point as opposed to an imaginary point. Because the elementary volume has a dimension along the pencil beam, each of the channels already referred to has parallel sides and in fact the channels can be formed by a series of baffles which have a cross-section, in a plane perpendicular to the plane of the pencil beam, of a trapezoid. Other baffle cross-sections will be apparent from a review of the remaining portions of the application.

BRIEF DESCRIPTION OF THE DRAWINGS

The present invention will now be described in further detail so as to enable those skilled in the art to make and use the same, in the following portions of this specification when taken in conjunction with the attached drawings wherein.

DETAILED DESCRIPTION OF PREFERRED EMBODIMENTS

Figure 1:
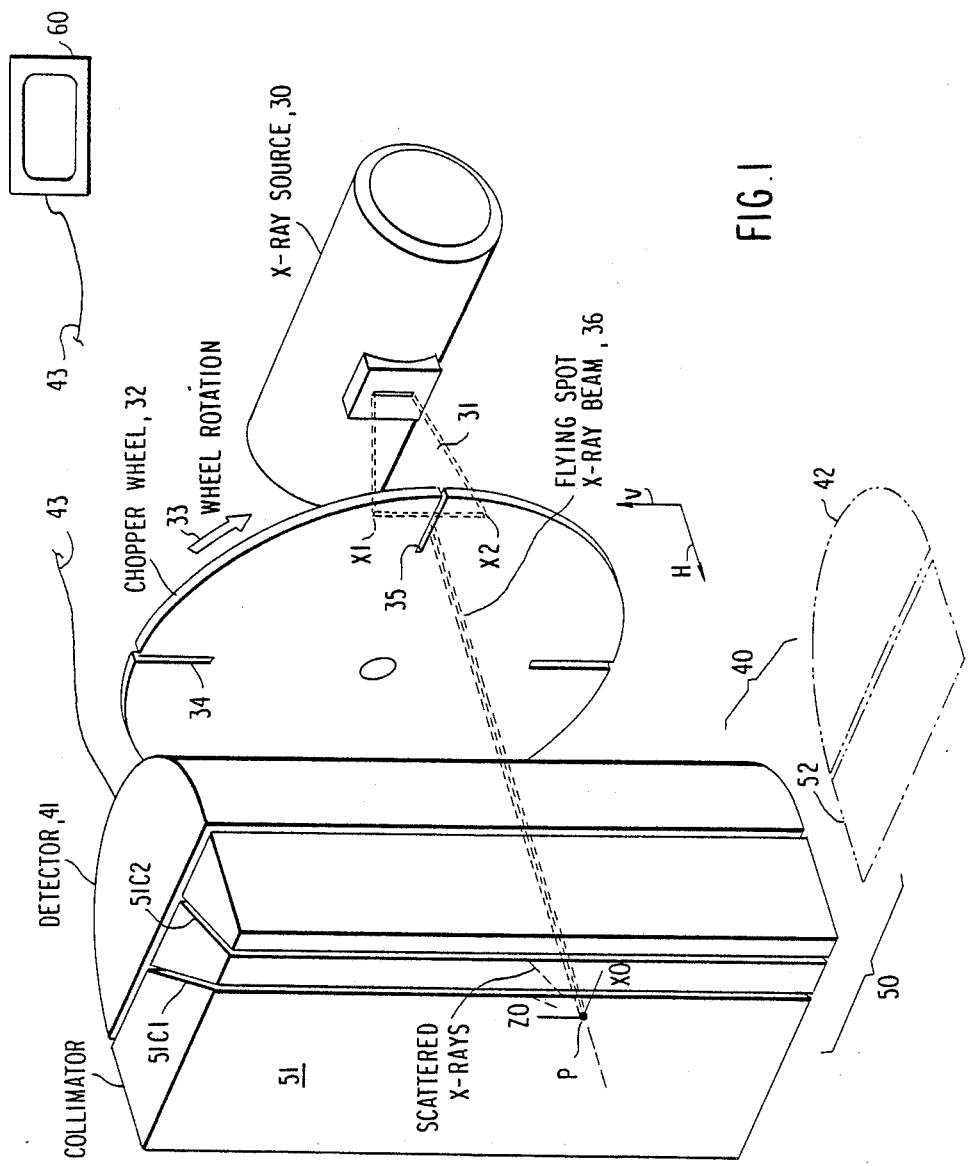
FIG. 1 is a three-dimensional view of the major components of an embodiment of the invention.

As shown in FIG. 1, the major elements of the invention include an x-ray source 30 emitting a fan beam 31. The fan beam 31 intercepts a rotating chopper wheel 32. The chopper wheel is composed of radiation opaque material but it has a plurality of slits, such as slits 34 and 35. As the chopper wheel rotates, in the direction of the arrow 33, the different slits intersect the fan beam 31. When a slit intersects the fan beam, a pencil beam 36 is emitted, and as the wheel 32 rotates, the pencil beam 36 is swept to traverse a line in space. As shown in FIG. 1, where the arrows H and V respectively define horizontal and vertical planes, respectively, the sweep is vertical, i.e. as the wheel rotates in the direction 32, the sweep begins when a slit first intersects the fan beam at the point x1, and the pencil beam 36 is swept vertically downward and terminates when the slit intersects the fan beam at the point x2. The cooperation between the x-ray source and the chopper wheel is more fully described in U.S. Pat. No. Re. 28,544, assigned to the assignee of this application.

The foregoing elements are arranged so that the pencil beam 36 intersects an object to be imaged (which is not illustrated in FIG. 1). The pencil beam 36 intersects the object to be imaged along a path which passes through the object. The goal of the invention is to produce a tomographic image of a selected slice of the object, and for purposes of description we will assume that the point P, in FIG. 1, is that point in the selected slice which coincides with the path of the pencil beam 36 at that portion of the beam's sweep frozen in the illustration. Depending on the composition of the object at the point P, radiation is scattered, and indeed radiation is scattered by material within the object lying along the entire path of the pencil beam 36. Located between the object (which is not illustrated) and the components already described is a line collimator 50, in the embodiment shown in FIG. 1 consisting of line collimator elements 51 and 52, the latter shown in phantom to avoid obscuring the other elements. Adjacent the line collimator elements 51 and 52 is radiation detector 40 comprising radiation detector elements 41 and 42. These elements can for example comprise conventional scintillator crystals for converting incident x-ray energy into optical energy and converting the optical energy into electrical signals. The detector elements 41 and 42 are arranged so as to produce, at any instant in time, a single electrical signal which is coupled over a conductor 43 to an imaging device 60 such as a cathode ray tube or hard copy printer or preferably to a computer which records the detector signals and is then used to drive the CRT 60 or printer.

In order to develop an image of the selected slice, radiation scattered by the point P must be preferentially detected as opposed to radiation scattered by other portions of the object lying along the path of the pencil beam 36. To this end, the collimator elements 51 and 52 each have a plurality of channels therein such as the channels 51C1 and 51C2 shown in FIG. 1. While FIG. 1 only shows two channels, for clarity, there are actually many more channels to collect as much scattered radiation as possible. Practical limitations and considerations of efficiency dictate collecting as much radiation as practical. Aside from the channels, the collimator elements 51 and 52 are composed of radiation absorbing material. The baffles comprising this radiation absorbing material may be extremely thin because the radiation to be excluded must either traverse the baffles at a small angle resulting in a large attenuation, or must traverse many baffles if the angle is large. This allows the design of an extremely efficient collimator which accepts a large fraction of the energy in the desired slice and rejects energy emanating from other regions. As a result, the only radiation "seen" by the detector elements 41 and 42 is that radiation which travels through one of the channels in the collimating elements 51 and 52. As will be described below, each of the collimating elements has a field of view which is defined by a bounded line located a fixed distance from a reference surface of the collimator elements 51 and 52. The sweep of the pencil beam is arranged so that it sweeps entirely this bounded line. Since the pencil beam 36 sweeps as a function of time, then as a function of time the signals produced by the detector elements 41 and 42 will correspond to different elementary volumes lying along the bounded line. As can be seen in FIG. 1, the channels 51C1 etc. are substantially planar to define channel planes. As will be seen below in connection with FIG. 3, these channel plane intersect the selected slice in a bounded line 11 along which the pencil beam 36 traverses as a function of time.

Figure 2:
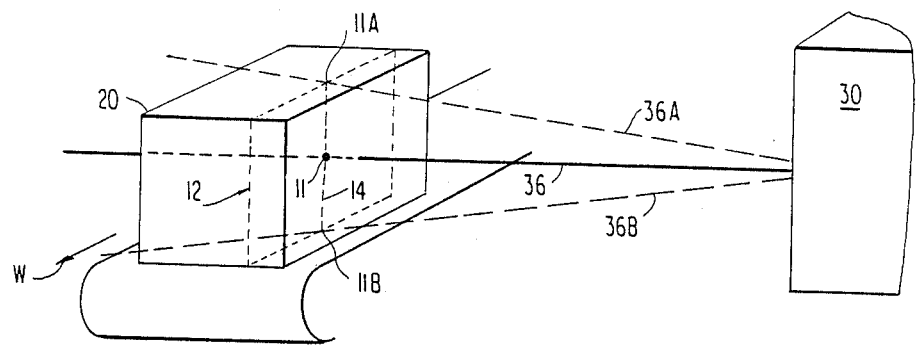
FIG. 2 is a schematic illustration showing some of the components which is useful in explaining the theory of operation of the invention.

Reference is made to FIG. 2 which shows operation of the invention more clearly than can be seen in FIG. 1. In Fig. 2, the same reference characters are employed to identify identical apparatus. FIG. 2 shows the object 20 and for the case of FIG. 2 the selected slice is the plane 12. Not shown in FIG. 2 are the line collimating elements 51, 52, nor the detecting elements 41, 42. As shown in FIG. 2, the pencil beam 36 intersects the selected slice 12 in the point 11. The sweep of the pencil beam 36 extends from the dashed line 36A to the dashed line 36B, and the pencil beam 36 repeatedly traverses this region and as a result the pencil beam intersects the selected slice 12 at one extreme of the sweep at the point 11A and the other extreme of the sweep at the point 11B. Thus, the sweep of the pencil beam 36 extends over the bounded line 14 which lies in the selected slice 12. As will be described below, it is only radiation scattered by elementary volumes of the object lying along or centered on the bounded line 14 which will contribute to the image. It should be apparent to those skilled in the art that if the radiation detectors 41 and 42 can be screened from all radiation except that which is scattered from volumes lying along the line 14, then the image produced by signals generated by the detected radiation will provide an image of the object 20 corresponding to those portions of the object 20 adjacent the line 14. Furthermore, the image can be expanded to correspond to the entire selected slice 12 by translating the object 20 relative to the source 30/detectors 41/42. The manner in which this is achieved is explained more fully below.

Figure 3:
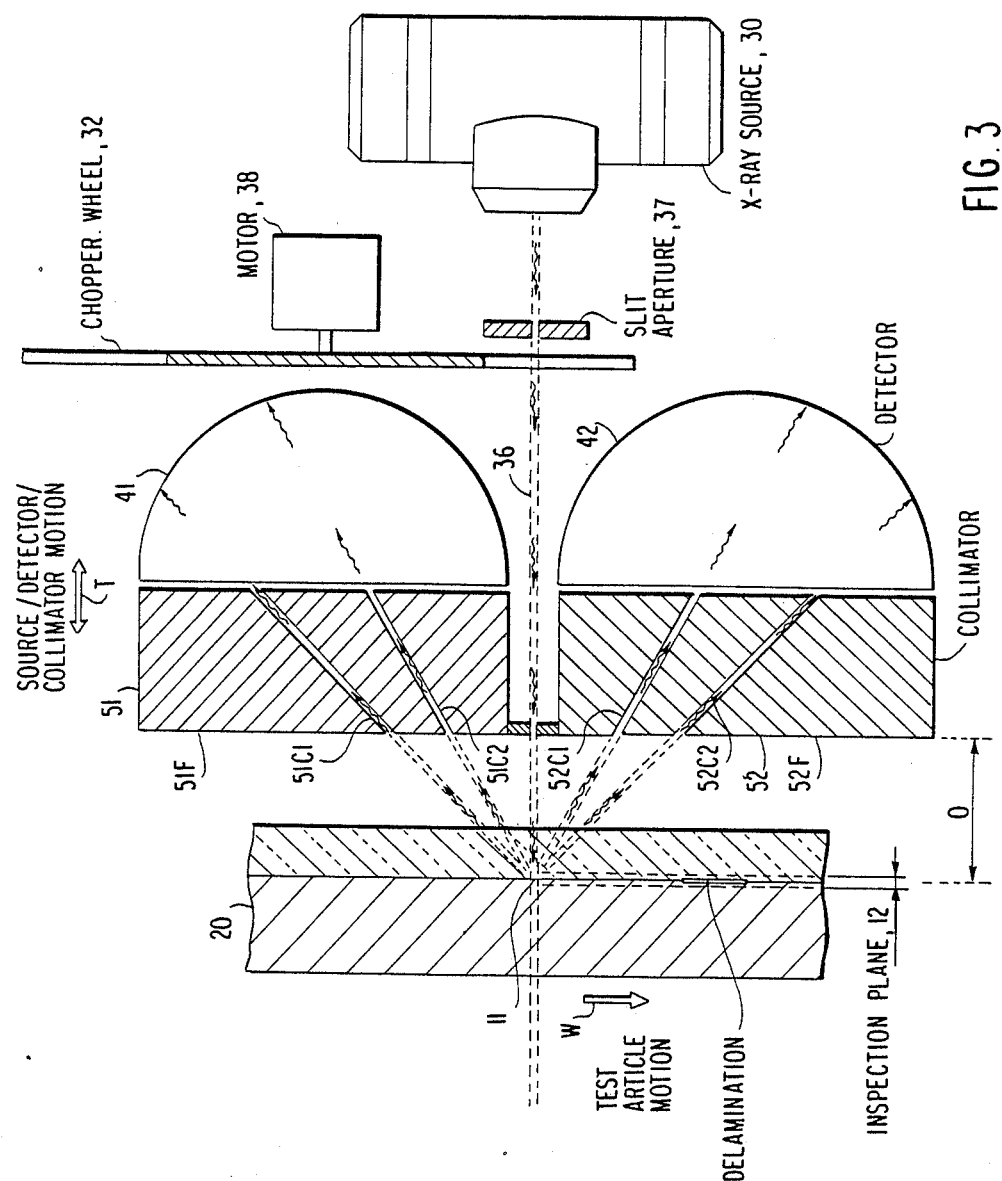
FIG. 3 is a section of the components of FIG. 1 and showing in addition the object being imaged and the selected slice of the object, for a specific application of the invention in which the selected slice is in the form of a plane.

Referring now to FIG. 3, which is a cross-section of FIG. 1 but to which has been added a section of the object 20, Fig. 3 shows the x-ray source 30 in relation to the chopper wheel 32 and reveals the presence of a slit aperture 37 (which is not shown in FIG. 1) all for forming the sweeping pencil beam 36. FIG. 3 shows the path of the pencil beam 36 through the test object 20. Because the motion of the pencil beam 36 is perpendicular to the plane of the drawing, that motion is not visible in the drawing. FIG. 3 does illustrate that the line collimator consists of line collimator elements 51 and 52, each located on a different side of the pencil beam 36. Likewise, the radiation detector comprises elements 41 and 42, also separated by the pencil beam 36. While this is preferred for efficiency purposes, it should be apparent that the line collimator and detector need not extend on both sides of the pencil beam. Scattered energy from the object 20, resulting from the illumination provided by the pencil beam 36, is firstly capable of being scattered by any portion of the object lying within the path of the pencil beam 36, and that energy may be scattered throughout the entire 360° solid angle surrounding any scattering point. However, because of the presence of the line collimator 50, and its composition as a radiation absorber, only scattered energy traversing a channel within the line collimator can reach the radiation detector. As is apparent from FIG. 3, all of the channels 51C1, 51C2, 52C1 and 52C2 "look" at a bounded line 14, the line in FIG. 3 represented by the point 11, but reference to FIG. 2 illustrates that that line is the line 14. While any point along the line 14 can contribute scattered energy which will be "seen" by the detector, because of the sweeping motion of the pencil beam 36, only one point (or an elementary volume) along the line 14 is illuminated at any time. Accordingly, at any time only scattered energy from a single elementary volume of the object 20 can be "seen" by the detector. However, as the pencil beam 36 sweeps as a function of time, a sequence of signals derived from the scattered energy will be capable of representing those elementary volumes lying along the bounded line 14. Furthermore, as the object 20 is translated, in the direction of the arrow W (with all other components stationary) the bounded line will actually trace out the selected slice 12.

The location of the selected slice within the object 20 is determined in part by the angle the various channels make with the path of the pencil beam 36 and the distance between the mouth of the channel in the line collimator and the path of the pencil beam 36. As is evident from FIG. 3, each of the channels lies along a line which intersects the pencil beam at a single, common point. Thus, the location of the selected plane 12 is always a fixed distance from a reference point on the line collimator, for example the front face 51F and 52F. It should be apparent therefore that if, using the apparatus shown in FIG. 3, we wanted to image a different selected slice, then we translate the collimator relative to the object in the direction of the arrow T. It should be emphasized that to image a particular slice in accordance with the invention, there is no requirement that the source 30, detector 40 or collimator 50 be moved during the course of exposure. In order to vary the location of the selected slice, however, the position of the collimator relative to the object may be altered. Desirably, at least the detector undergoes the same change of position as does the collimator in order to maintain the collimator/detector adjacent one another. In some cases, it may be desirable and/or preferable to move the source and chopper wheel along with the collimator/detector, although it should be apparent that is not at all essential.

To quantify the image produced by the invention, consider a line collimator located between a detector and an edge of an object, where the distance from detector to object surface is L. Consider a slice located within the object a distance x from the same surface, with slice thickness Δx. Consider:

$I_0$ = incident flux (rads or phontons/cm$^2$)

The flux received by the detector is:

$$= [I_0][e^{-\int_0^x \mu_{TOT}(x)dx}][\mu_{sc+fl}(x)\Delta x][AWO][GF]$$

where the total factor is the attenuation of the beam on the way in. $\mu_{TOT}(x)$ is the total attenuation coefficient at the depth x, $\mu_{sc+fl}(x)\Delta x$ is the fraction of the scattered and fluorescent x-rays emitted at depth x from Δx AWO = attenuation on the way out is the average attenuation for scattered x-rays moving back to the detector, GF = refers to geometrical factors dictated by the solid angle subtended by the detectors at Δx and the transmission ratio of the line collimator.

Therefore, the image which has been referred to is the product of the second and third factors, the second factor represents attenuation of the beam in reaching the depth x, and the third factor is a result of material within the slice. In a sense we see the "slice" through a filter whose density is determined by the material in line with beam 36. Since the image is a product and not a sum, the desired image will show well. In many NDT applications the second factor is constant or near constant. In medical applications, the second factor is usually due to attenuation of soft tissue which is either approximately constant or slowly varying. Even in the case of lung tissue visualized behind the rib cage, the shadows of the ribs will be visible but lesions will be seen at high signal to noise ratios.

In the foregoing description it should be apparent to those skilled in the art that once the detected signals are converted to electrical form, an image can be generated (via CRT or hard copy printer) in an entirely conventional manner.

From another point of view, the field of view of the collimator 42/43 (a total field of view) is merely the sum of the field of view of each channel. That total field of view is partially shown in FIG. 3 as the dashed line extensions of the channels 51C1, 52C1, etc. within the object 20. FIG. 3 only partially shows the total field of view since the dashed lines must be extended through the object 20 to completely show the total field of view. FIG. 3 readily illustrates that the collimator's total field of view intersects the plane defined by the sweeping pencil beam 36 in the bounded line 14, already referred to, and seen in FIG. 3 as point 11.

Figure 4:
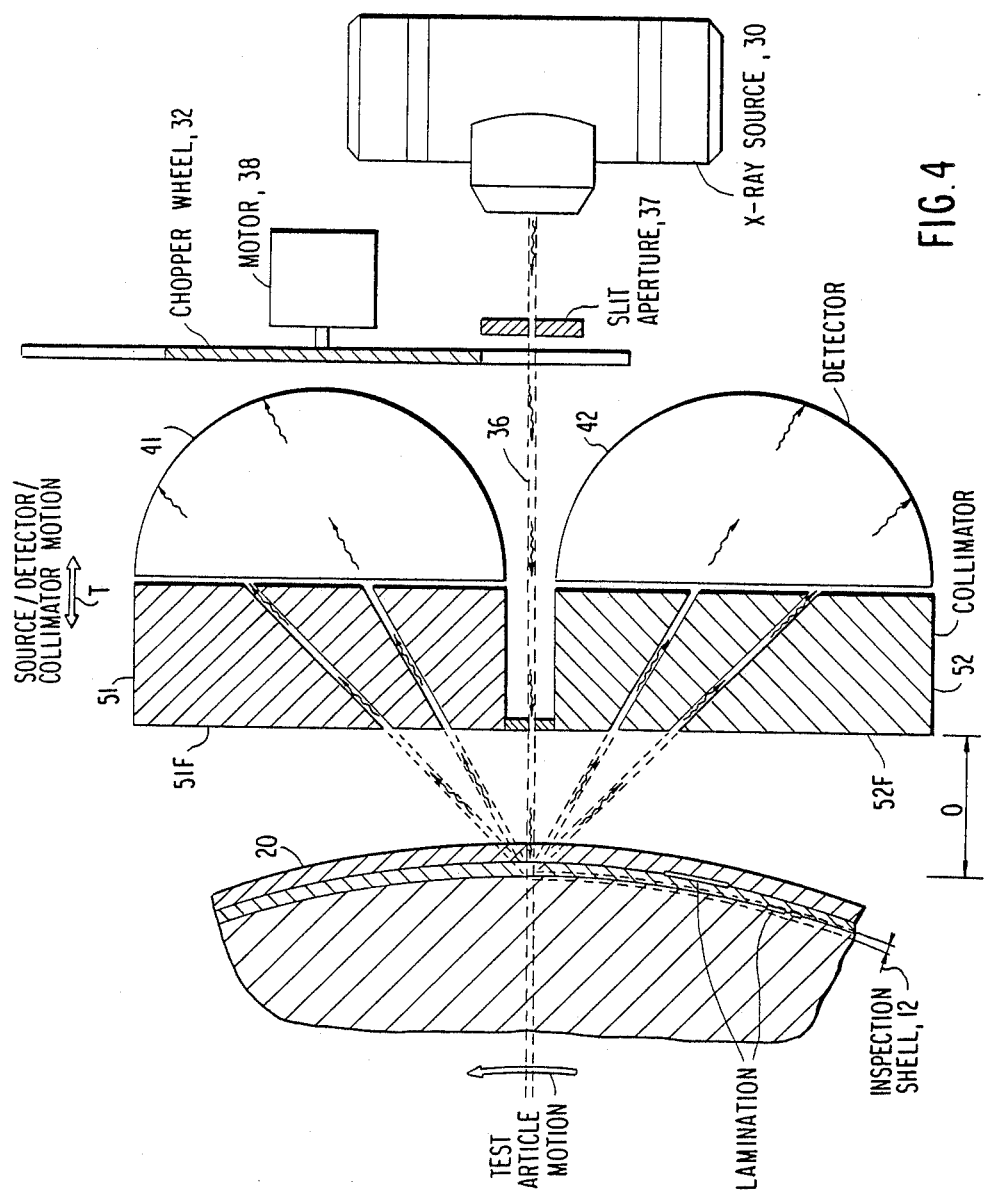
FIG. 4 is a view similar to FIG. 3 except that in FIG. 4 the selected slice is a cylindrical surface.

FIG. 4 is entirely similar to FIG. 3 except that the motion of the object 20, during the course of image generation is circular rather than linear. More particularly, just as in the case of FIG. 3, the bounded line or preferential line of visibility is located a distance O from the reference surface of the collimator. In the case shown in FIG. 4, the selected slice is in the form of a right circular cylinder, denoted by the reference "Inspection Shell". To achieve an image of the selected slice which is a right circular cylinder, rather than translating the object 20 (as shown in FIG. 3), the object 20 is rotated about an axis which is parallel to the bounded line 14, but offset therefrom. Those skilled in the art will understand how, with this type of motion, the bounded line 14 will trace out the surface of a right circular cylinder and therefore the image produced on the display 60 will be that of a slice corresponding to that right circular cylinder.

Figure 5:
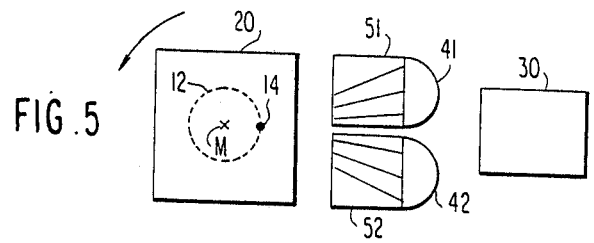
FIG. 5 is a section of FIG. 4 showing development of the complete slice relative to the object being imaged.

FIG. 5 illustrates this effect in a more schematic fashion. FIG. 5 shows the x-ray source 30, the line collimator 50 comprising line collimator elements 51 and 52, and the radiation detector 40 comprising detector elements 41 and 42. The object 20 is shown as square in cross-section, although it should be apparent that the cross-section of the object is relatively immaterial. In the section of FIG. 5, the bounded line 14 is represented by the point 14. The desired selected slice is shown as a dotted line 12. To achieve an image of a right circular slice, the object 20 is rotated about the axis M, which is a line parallel to the bounded line 14 but offset therefrom. Non-circular right cylindrical shapes are generated by rotation about an axis which does not lie within the plane defined by motion of pencil beam 36.

Figure 6:
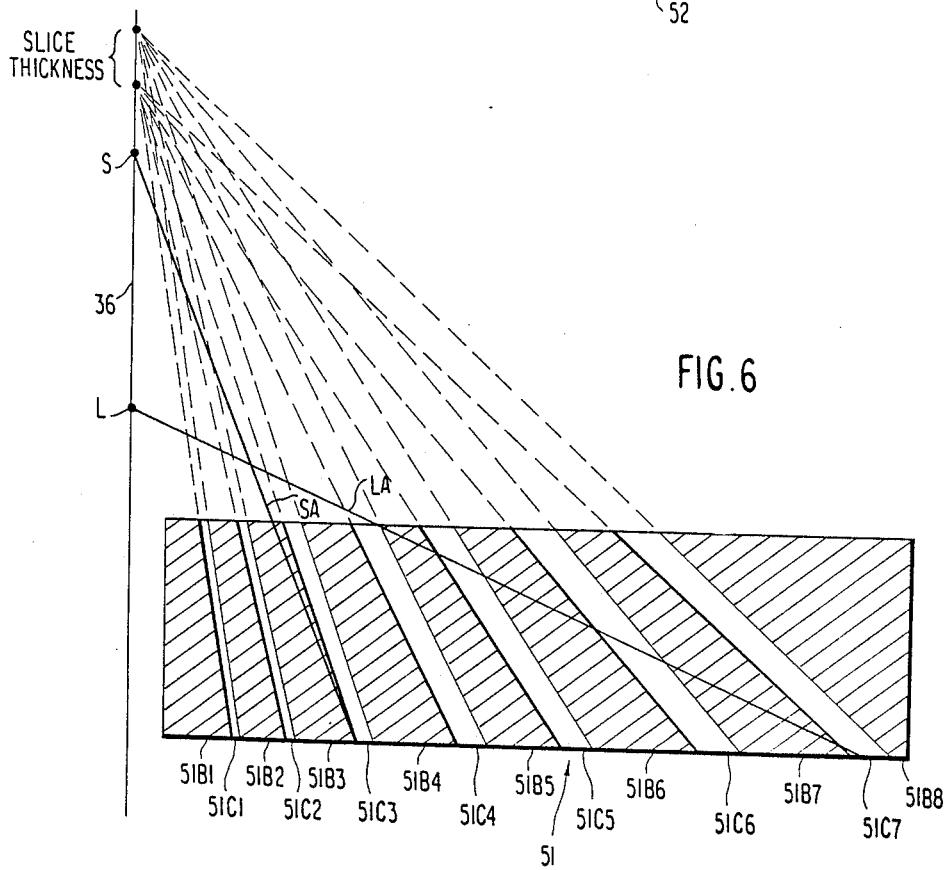
FIG. 6 is a detail of one embodiment of one element of the line collimator.

In the preceding description the intersection between the pencil beam 36 and the selected slice 12 has been variously referred to as an elementary volume or a point; it should be apparent that where a "point" has been referred to, that is a theoretical construct and in fact since the pencil beam 36 has finite dimensions, so too will the intersection of the pencil beam and the selected slice 12 have finite dimensions, in at least two dimensions. Furthermore, preferably the elementary volume also has a finite dimension along the length of the path 36. This dimension is represented in Fig. 6 by the notation "slice thickness". FIG. 6 shows a cross-section of an embodiment of a line collimating element 51. As shown in FIG. 6, the line collimating element has a cross-section in a plane perpendicular to the plane defined by the sweep of the beam 36, which includes a plurality of channels defined between a series of baffles. Actually, the line collimator has the same cross-section in many planes perpendicular to the plane defined by the sweeping pencil beam. FIG. 6 shows channels 51C1–51C7 formed by baffles 51B1–51B8. The baffles of course are comprised of radiation absorbing material such that radiation scattered from scattering points along the path 36 can only reach the detector side of the collimator 51 by traversing a path which passes through one of the channels. As is seen from FIG. 6, every path through any channel originates along the "slice thickness" and as a result the detector 40 can only "see" scattering points in this region. To illustrate the point made above concerning the size of the baffles, consider radiation scattered from the points L and S. Radiation scattered from the point L makes a large angle (line LA). Respect to the radiation scattered from along the preferential line. The energy scattered from the point L then (See FIG. 6) traverses three baffles and thus the thickness of a single baffle need not be sufficient, by itself to exclude this undesired energy. Radiation scattered from the point S makes a small angle (line SA) with respect to radiation scattered from along the preferential line. While this energy traverses only a single baffle (51 B3) it does so along almost the entire length. Here too, the thickness of the baffle need not be selected to exclude the energy.

FIG. 6 is drawn for the case in which the sides of two baffles adjacent a channel are parallel, and the baffles, or at least the intermediate baffles, have a cross-section of the form of a trapezoid (a closed four-sided figure with a pair of parallel sides and a pair of non-parallel sides).

Figure 7:
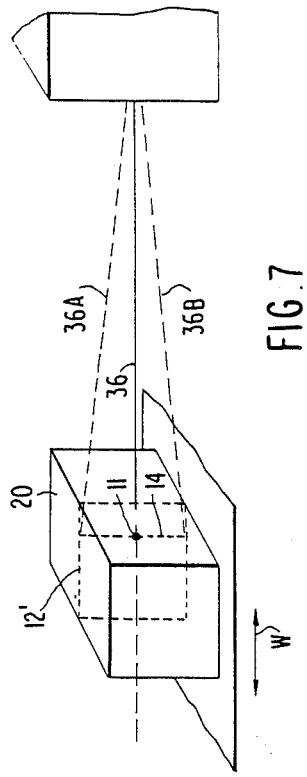
FIG. 7 is similar to FIG. 2 for a different embodiment of the invention.

The preceding description has been relative to those cases wherein motion of the object 12 is mutually perpendicular to the plane of the beam 36 and the bounded line 14, however, that is not the only type of linear motion that can be employed. More particularly, referring to FIG. 7 (which is similar to FIG. 2) note that in the orientation of FIG. 7 the direction of motion W is parallel to the plane of the path of the pencil beam 36. In FIG. 7, just as in FIG. 2 the collimator/detector is not illustrated for clarity, but the bounded line 14 is shown. The selected slice 12' (in this case coextensive with the plane defined by the sweeping motion of the pencil beam 36) is traced out by the bounded line 14 moving relative to the object 20 in the direction W.

Although the preceding description has been relatively schematic, it should be apparent that the required motion of the object 20 is relatively simple (linear or circular motion has been described) and those skilled in the art are readily capable of providing apparatus to effect that motion without further description. Likewise, the motion of the chopper wheel (effected by the motor 38) is also well-known. While the invention requires the use of a radiation detector to translate the scattered x-ray energy into electrical signals, processing electronics and display hardware to generate an image from those signals in coordination with the sweeping motion of the pencil beam and whatever motion of the object 20 has been selected, those of ordinary skill in the art can readily provide this apparatus without further description.

Furthermore, while the preceding description has described cases in which the selected slice 12 was generally planar (FIGS. 2 and 7) or the surface of a right circular cylinder (FIG. 5), there is no inherent limitation on the form of the selected slice except that it must be a surface generated by a moving line. Furthermore, the line, while it intersects the pencil beam 36 at all times, need not be perpendicular thereto. Accordingly, the selected slice can have the form of any cylindrical surface, including conical surfaces.

The preceding description has included a description of a mechanical chopper to form and sweep the pencil beam such as that disclosed in U.S. Pat. No. Re. 28,544. However, it is within the spirit and scope of the invention to employ other apparatus for forming and sweeping a pencil beam of x-radiation.

It is a particular advantage of the invention that the radiation detector can be shielded from energy scattered from all points except those lying on a preferential line. By using such a line collimator, any requirement for motion of the collimator during the course of image generation is eliminated. For example, the Lale publication cited above, which is generally directed at tomographic imaging and employs a sweeping pencil beam, suggests the use of a point collimator, in the form of a conical collimator. Accordingly, Lale's collimator must be moved as the beam sweeps. This requirement imposes severe burdens on the speed and complexity of the apparatus.

Figure 8:
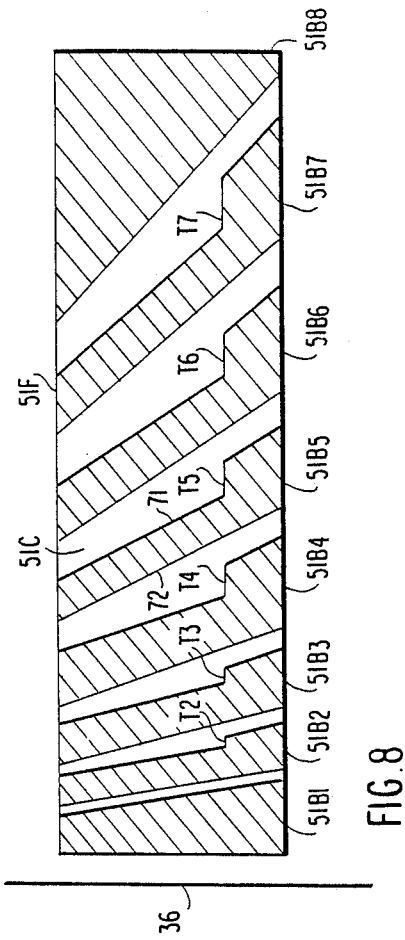
FIG. 8 is a detail of another embodiment and FIG. 9 is useful in explaining the relation between beam breadth and slice thickness.

While FIG. 6 shows one embodiment of the line collimator, FIG. 8 shows an alternate and for some applications a preferred embodiment. The line collimator of FIG. 8 has baffles with generally parallel sides and a transition generally parallel to the collimator face 51F, such as transitions T2-T7. This baffle shape may be simpler to manufacture and exploits the collimator property described in connection with the lines LA and SA (see FIG. 6).

Figure 9:
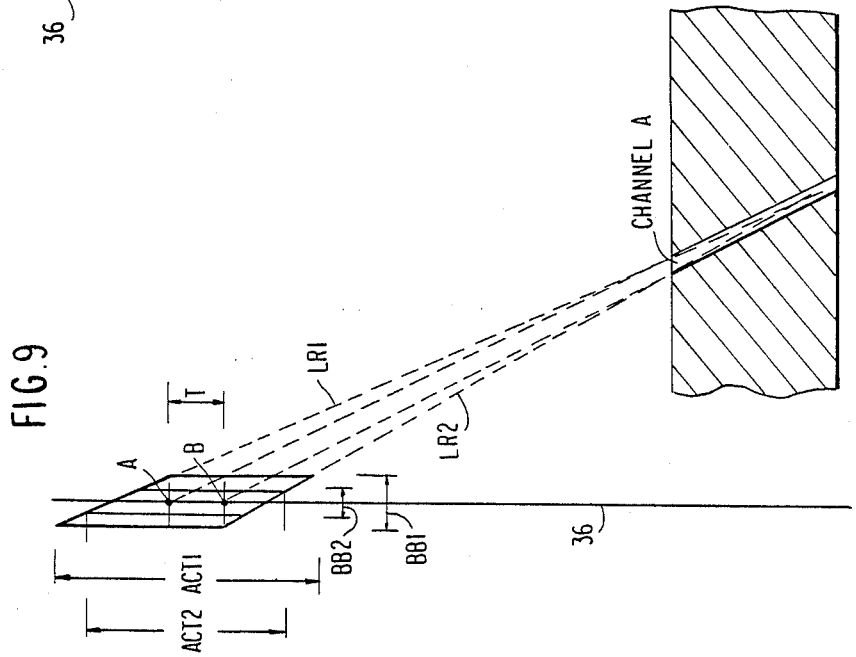

The dimension of an elementary volume is constrained by a number of requirements. In order to "see" a feature of an object, the presence of the feature must be manifested by scattered or fluorescent energy which is detected. This requires a minimum threshold of photons which requires the beam cross-section to have finite dimensions. For convenience, the term length of the beam section is taken as that dimension of the beam cross-section measured in the plane defined by the sweep, and beam breadth is the other dimension of the cross-section. FIG. 9 shows the pencil beam 36 relative to a typical channel A, of the line collimator, shown in section, similar to FIGS. 6 and 8. The channel A is dimensioned for a nominal slice thickness T, i.e. the sides of channel A intersect the points A, B along beam axis 36. When we consider a real beam, of breadth BB1, we find the actual slice thickness is ACT1. The actual slice thickness is found by constructing the path of limit rays LR1 and LR2, these are the rays which are derived from the outermost extremity of beam breadth and just graze edges of channel A. On the other hand, ACT2 represents actual slice thickness if beam breadth is reduced to BB2. As indicated above, we need real beam cross-section (non-zero) but as shown in FIG. 9 we pay a penalty for increasing beam breadth, in increasing actual slice thickness. As actual slice thickness increases the resolution of the image is degraded. Where the goal is to see a region of the object which is thin in the direction of slice thickness, then I prefer a beam whose cross-section is asymmetrical, one with beam cross-section length greater than breadth. For example, a beam cross-section of 40 $mm^2$ could be obtained by a cross-section of 6.3 mm beam section length and breadth. However, I prefer one with beam section length of 20 mm and breadth of 2 mm; a ratio of section length to breadth of about 10 to 1 or greater.

In accordance with the invention, the source of radiation has its energy level selected in accordance with the objects being imaged. For example, in medical applications typical x-ray energies would be in the low kilovolt range, security applications might require similar energy levels, non-destructive testing in which the objects being imaged are reltively larger and more dense would correspondingly require higher energy levels.

It is a particular advantage of the invention that the baffles of the line collimator 50 can be relatively thin, even for high illumination energies. This follows from the fact that non-preferred radiation (scattered from volumes far from the preferential line 14) will intersect many baffles (not merely one), and the effect of the line collimator is the cumulative effect of all the baffles intersected by the non-preferred energy.

In all embodiments described above, the reference surface of the collimator and the radiation detector have planar form or active surfaces. However, the collimator could have a reference surface in intersecting planes so long as all reference surfaces (and associated collimator elements) defined a single bounded preferential line.

One of the prime advantages of the invention is the line collimator. It is ideally suited for detection of scattered or fluorescent energy which can come off at many angles, but yet can focus on a preferred region. By increasing the size (cross-section) of the line collimator in a plane perpendicular to the plane of the sweep and perpendicular to the pencil beam at the mid-point of its sweep, we increase the solid angle "seen" by each region of the slice. In one embodiment actually constructed, the solid angle subtended by the detector was about ⅓π and the line collimator was constructed to pass about 60% of the selected energy, so that the apparatus collected about 10% of the scattered energy for a low energy incident beam. As mentioned elsewhere, the line collimator is not restricted to the shapes of FIGS. 1, 3, 4 and 5, which have reference surfaces (51F, 52F) in one plane. In other embodiments, the line collimator can have reference surfaces in intersecting planes so long as the channels are oriented to focus on a single bounded preferential line. Each embodiment so far described has had a preferential line parallel to the reference surface 51F and 52F. That is not essential, as will now be described. Consider, as a teaching example, the effect of tilting the line collimators (see Fig. 1), keeping the base fixed, but tilting 51 to rotate it about its base in the −x direction. This has the effect of rotating the preferential line, in the sweep plane, about an axis in the inspection plane (see FIG. 3) so that in the sweep plane the preferential line is no longer parallel to the reference surfaces 51F, 52F. A corresponding tilt is provided to element 52 but in the opposite direction, i.e. +x. In actual practice the collimators are not tilted, but instead the orientation of the channels is similarly rotated. The result, as stated, is a preferential line no longer parallel to the reference surfaces 51F, 52F. If we refer to the -x rotation of channels in 51 and the +x rotation of channels in 52 as a tilt of one sense, clearly we also have available tilting in the opposite sense, i.e. +x rotation of channels in 51 and −x rotation of channels in 52. The only difference is whether the preferential line approaches or recedes from the reference surfaces 51F, 52F as the pencil beam sweeps down, for example.

Thus, it should be apparent that many changes can be made to the described embodiments falling within the spirit and scope of the invention which is to be construed in accordance with the attached claims.

I claim:

1. A device useful in producing a tomographic image of a selected slice of an object to be examined comprising:
    a source of penetrating radiation,
    sweep means for forming energy from said source into a pencil beam and for repeatedly sweeping said pencil beam over a line in space to define a sweep plane,
    first means for supporting an object to be examined so that said pencil beam intersects said object along a path passig through said object and said selected slice,
    line collimating means for filtering radiation scattered by said object, said line collimating means having a field of view which intersects said sweep plane in a bounded line so that said line collimating means passes only radiation scattered by elementary volumes of said object lying along said bounded line, said line collimating means including a plurality of channels such substantially planar in form to collectively define said field of view, said channels oriented so that said pencil beam sweeps along said bounded line as a function of time, and
    radiation detector means responsive to radiation passed by said line collimating means 2. The apparatus of claim 1 in which said first means includes means providing relative motion between said object and said radiation detector means and said line collimating means.

3. The apparatus of claim 2 in which said selected slice is planar and said relative motion is linear.

4. The apparatus of claim 2 in which said selected slice is a cylindrical surface and said motion is circular about an axis parallel to, and offset from said bounded line.

5. The apparatus of any of claims 1-4 in which said line collimating means and said radiation detector means lie between said source and said object.

6. The apparatus of claim 5 in which:
    said radiation detector means includes first and second radiation detector elements located on different sides of a path traversed by radiation from said source to said object.

7. The apparatus of claim 5 in which:
    said line collimating means includes first and second line collimating elements located on different sides of a path traversed by radiation from said source to said object.

8. The apparatus of claim 1 in which said line collimating means includes:
    a radiation absorbing structure which has substantially similar cross-sections, in planes perpendicular to a plane defined by the sweeping motion of said pencil beam, including said plurality of channels, each channel lying along an imaginary line terminating at the intersection of said pencil beam and said selected slice and extending through a first face of said line collimating means, closer to said object than to said detector means, to a second face of said line collimating means closer to said detector means than to said object.

9. The apparatus of claim 8 including means for supporting said radiation detector means adjacent said line collimating means to provide, through said channels, a path for radiation scattered by said elementary volumes.

10. The apparatus of claim 8 in which said channels have parallel sides.

11. The apparatus of claim 8 in which said channels are separated by baffles, said baffles comprised of radiation absorbing material.

12. The apparatus of claim 11 in which at least one of said baffles has a first pair of straight parallel sides and a second pair of parallel sides, at least one of which includes a transition region substantially parallel to said first pair of sides.

13. The apparatus of claim 1 which further includes slice adjusting means for moving said line collimating means toward or away from said object to adjust a location of said selected slice relative to a surface of said line collimating means.

14. The apparatus of claim 1 in which said sweep means includes:
    a fixed slit in a path of radiation emitted by said source to form a fan beam,
    a chopper wheel rotated about an axis parallel to a plane defined by sweeping motion of said pencil beam, said chopper wheel including slit means for forming a sweeping pencil beam as said chopper wheel rotates moving said slit means to intersect said fan beam.

15. The apparatus of claim 1 wherein said sweep means includes means for forming a pencil beam with an asymmetrical cross-section.

16. The apparatus of claim 1 wherein said sweep means includes means for forming a pencil beam with beam breadth, measured perpendicular to a plane defined by said sweeping motion, and beam length, measured in said plane, wherein a ratio of beam length to beam breadth is substantially greater than unity.

17. The apparatus of claim 16 in which said ratio is about 10 or greater.

18. A method useful in generating a tomographic image of a selected slice of an object comprising the steps of:
providing a source of penetrating radiation,
forming a pencil beam from energy emitted by said source and repeatedly sweeping said pencil beam over a line in space,
supporting an object to be examined so that said pencil beam intersects said object along a path passing through said object and said selected slice,
filtering radiation scattered by said object to pass only radiation scattered by elementary volumes of said object lying along a line defined by a succession of intersections between said path and said selected slice by interposing a radiation absorbing structure with plural, substantially planar, radiation transmitting channels between said object and a radiation detector, said channels interposed relative to the sweeping pencil beam so that said pencil beam sweeps along said line as a function of time, and
detecting radiation passed by said filtered step.

19. The method of claim 18 in which said supporting step includes the step of providing relative motion between said object and said line in space which is swept by said pencil beam.

20. The method of claim 19 in which said selected slice is planar and said relative motion is linear.

21. The method of claim 19 in which said selected slice is a cylindrical surface and said motion is circular about an axis parallel to, and offset from said line defined by said succession of intersections.

22. The method of claim 18 which includes the further step of moving said object to adjust a location of said line defined by a succession of intersections between said path and said selected slice.

23. Apparatus useful for tomographic imaging of a selected slice of an object comprising:
radiation detector means providing, at any time a single output signal indicative of radiation reaching all portions of said detector means,
collimating means adjacent to said radiation detector means with a field of view to pass to said radiation detector means scattered energy originating within said field of view, said collimating means including a plurality of channels each substantially planar in form to collectively define said field of view,
a source of penetrating radiation,
sweep means for forming radiation from said source into a pencil beam and for sweeping said pencil beam over a line in space so as to define a sweep plane, said sweep plane intersecting said field of view in a bounded line, said sweep means sweeping said pencil beam over said bounded line as a function of time,
means for supporting an object to be imaged so that said bounded line lies within a selected slice which is to be imaged,
means for providing relative motion between said object and said collimating means so that, as a function of time said bounded line traces said selected slice, and
image means responsive to a time sequence of output signals for forming an image.

24. The apparatus of claim 23 in which said selected slice is planar and said relative motion is linear.

25. The apparatus of claim 23 in which said selected slice is a cylindrical surface and said motion is circular about an axis parallel to, and offset from said bounded line.

26. The apparatus of any of claims 23-25 in which said collimating means and said radiation detector means lie between said source and said object.

27. The apparatus of claim 26 in which:
said radiation detector means includes first and second radiation detector elements located on different sides of a path traversed by radiation from said source to said object.

28. The apparatus of claim 26 in which:
said collimating means includes first and second line collimating elements located on different sides of a path traversed by radiation from said source to said object.

29. The apparatus of claim 23 in which said collimating means includes:
a radiation absorbing structure which has a cross-section, in a plane perpendicular to a plane defined by the sweeping motion of said pencil beam, including a plurality of channels, each channel lying along an imaginary line terminating at the intersection of said pencil beam and said selected slice and extending through a first face of said collimating means, closer to said object than to said detector means, to a second face of said collimating means closer to said detector means than to said object.

30. The apparatus of claim 29 including means for supporting said radiation detector means adjacent said collimating means to provide, through said channels, a path for radiation scattered by a region within said object adjacent said bounded line.

31. The apparatus of claim 29 in which said channels have parallel sides.

32. The apparatus of claim 29 in which said channels are separated by baffles, said baffles comprised of radiation absorbing material.

33. The apparatus of claim 32 in which at least one of said baffles has a first pair of straight parallel sides and a second pair of parallel sides, at least one of which includes a transition region substantially parallel to said first pair of sides.

34. The apparatus of claim 32 which further includes slice adjusting means for moving said collimating means toward or away from said object to adjust a location of said selected slice relative to a surface of said collimating means.

35. The apparatus of claim 23 in which said sweep means includes:
a fixed slit in a path of radiation emitted by said source to form a fan beam,
a chopper wheel rotated about an axis parallel to a plane defined by sweeping motion of said pencil beam, said chopper wheel including slit means for forming a sweeping pencil beam as said chopper wheel rotates moving said slit means to intersect said fan beam.

36. The apparatus of claim 23 wherein said sweep means includes means for forming a pencil beam with an asymmetrical cross-section.

37. The apparatus of claim 23 wherein said sweep means includes means for forming a pencil beam with beam breadth, measured perpendicular to a plane defined by said sweeping motion, and beam length, measured in said plane, wherein a ratio of beam length to beam breadth is substantially greater than unity.

38. The apparatus of claim 37 in which said ratio is about 10 or greater.

39. The apparatus of claim 23 wherein:
   said collimating means comprises plural channels in a radiation absorbing structure, each of said channels being substantially planar to define plural channel planes, said channel planes intersecting said selected slice in said bounded line.

40. A device as recited in claim 1 in which said line collimating means comprises first and second collimating elements, each located opposite each other across said sweep plane, and said radiation detector means comprises first and second radiation detector elements, each located adjacent one of said first and second collimator elements and opposite each other across said sweep plane.

41. A device useful in producing a tomographic image of a selected slice of an object to be examined comprising:
   a source of penetrating radiation,
   sweep means for forming energy from said source into a pencil beam and for repeatedly sweeping said pencil beam over a line in space to define a sweep plane,
   first means for supporting an object to be examined so that said pencil beam intersects said object and said selected slice,
   second means for detecting radiation scattered, at any instant, by one of a group of selected volume elements in said slice, said second means subtending a large solid angle relative to said one selected volume element, said second means including:
   radiation detector means developing an any instant in time a single signal reflecting radiation impinging on said radiation detector means, and
   a collimator located between said object and said radiation detector means, said collimator including:
   a plurality of radiation transmitting channels collectively establishing a field of view which intersects said sweep plane in a preferential line which is a locus of a plurality of said selected volume elements so that said collimator passes radiation scattered by different elementary volume elements of said object lying along said preferential line as said sweep illuminates the different volume elements lying along said preferential line.

42. A device as recited in claim 41 wherein said collimator has a plane of symmetry which coincides with said sweep plane.

43. A device as recited in claim 41 wherein said collimator has a plurality of substantially planar radiation transmitting channels to define said field of view.

44. The apparatus of claim 41 in which said first means includes means providing relative motion between said object and said radiation detector means and collimator.

45. The apparatus of claim 44 in which said selected slice is planar and said relative motion is linear.

46. The apparatus of claim 44 in which said selected slice is a cylindrical surface and said motion is circular about an axis parallel to, and offset from said preferential line.

47. The apparatus of any of claims 41-46 in which said collimator and said radiation detector means lie between said source and said object.

48. The apparatus of claim 47 in which:
   said radiation detector means includes first and second radiation detector elements located on different sides of said sweep plane.

49. The apparatus of claim 47 in which:
   said collimator includes first and second collimator elements located on different sides of said sweep plane.

50. The apparatus of claim 41 in which said collimator includes:
   a radiation absorbing structure which has substantially similar cross-sections, in planes perpendicular to said sweep plane, including a plurality of channels, each said channel lying along an imaginary line terminating at the intersection of said pencil beam and said selected slice and extending through a first face of said collimator, closer to said object than to said radiation detector means, to a second face of said collimator closer to said radiation detector means than to said object.

51. The apparatus of claim 50 including means for supporting said radiation detector means adjacent said collimator to provide, through said channels, a path for radiation scattered by said elementary volume elements.

52. The apparatus of claim 50 in which said channels have parallel sides.

53. The apparatus of claim 50 in which said channels are separated by baffles, said baffles comprised of radiation absorbing material.

54. The apparatus of claim 53 in which at least one of said baffles has a first pair of straight parallel sides and a second pair of parallel sides, at least one of which includes a transition region substantially parallel to said first pair of sides.

55. The apparatus of claim 41 which further includes slice adjusting means for moving said collimator toward or away from said object to adjust a location of said selected slice relative to a surface of said collimator.

56. The apparatus of claim 41 in which said sweep means includes:
   a fixed slit in a path of radiation emitted by said source to form a fan beam,
   a chopper wheel rotated about an axis parallel to a plane defined by sweeping motion of said pencil beam, said chopper wheel including slit means for forming a sweeping pencil beam as said chopper wheel rotates moving said slit means to intersect said fan beam.

57. The apparatus of claim 41 wherein said sweep means includes means for forming a pencil beam with an asymmetrical cross-section.

58. The apparatus of claim 41 wherein said sweep means includes means for forming a pencil beam with beam breadth, measured perpendicular to said sweep plane, and beam length, measured in said sweep plane, wherein a ratio of beam length to beam breadth is substantially greater than unity.

59. The apparatus of claim 58 in which said ratio is about 10 or greater.

* * * * *